United States Patent
Cretoiu et al.

(10) Patent No.: US 8,460,517 B2
(45) Date of Patent: Jun. 11, 2013

(54) METHODS AND APPARATUSES FOR STEAM ADDITION TO A REBOILER COUPLED TO AN EXTRACTIVE DISTILLATION COLUMN FOR IMPROVED EXTRACTIVE DISTILLATION

(75) Inventors: Mircea Cretoiu, Sugar Land, TX (US); Andrei Cimpeanu, Houston, TX (US)

(73) Assignee: GTC Technology US LLC, Houston, TX (US)

( * ) Notice: Subject to any disclaimer, the term of this patent is extended or adjusted under 35 U.S.C. 154(b) by 198 days.

(21) Appl. No.: 12/706,937

(22) Filed: Feb. 17, 2010

(65) Prior Publication Data

US 2011/0048922 A1 Mar. 3, 2011

Related U.S. Application Data

(60) Provisional application No. 61/239,272, filed on Sep. 2, 2009.

(51) Int. Cl.
*B01D 3/00* (2006.01)

(52) U.S. Cl.
USPC .............. 203/76; 203/85; 203/92; 203/95; 203/96

(58) Field of Classification Search
CPC ........................................ B01D 3/00
USPC ............. 203/76, 83, 85, 92, 93, 95, 96, 97; 585/807
See application file for complete search history.

(56) References Cited

U.S. PATENT DOCUMENTS

| | | | | |
|---|---|---|---|---|
| 1,560,137 A | * | 11/1925 | Bernard | 208/341 |
| 3,083,148 A | * | 3/1963 | Mojonnier | 202/158 |
| 3,763,015 A | | 10/1973 | Morimoto et al. | |
| 5,330,624 A | * | 7/1994 | Ebert | 203/4 |
| 5,536,856 A | | 7/1996 | Harrison et al. | |
| 5,849,982 A | | 12/1998 | Lee et al. | |
| 5,877,385 A | * | 3/1999 | Lee et al. | 585/807 |
| 6,515,187 B1 | | 2/2003 | Schon et al. | |
| 6,781,026 B2 | | 8/2004 | Lee | |
| 7,326,323 B2 | * | 2/2008 | Mason et al. | 203/1 |
| 2006/0124544 A1 | | 6/2006 | Wills | |
| 2009/0056201 A1 | | 3/2009 | Morgan | |

OTHER PUBLICATIONS

Young, Lee W., International Search Report for PCT/US10/35891 as mailed Jul. 16, 2010 (2 pages).

* cited by examiner

*Primary Examiner* — Robert A Hopkins
(74) *Attorney, Agent, or Firm* — Winstead PC

(57) ABSTRACT

Methods and apparatuses for extractive distillation using internal addition of steam to an extractive distillation column from a reboiler are described herein. The apparatuses include an extractive distillation column, a reboiler (for example, a kettle reboiler) coupled to the extractive distillation column, and a steam input line. The steam input line is coupled to an internal steam sparger device of the reboiler. Methods utilizing the apparatuses to perform extractive distillation of a hydrocarbon feed stream are also described herein.

10 Claims, 1 Drawing Sheet

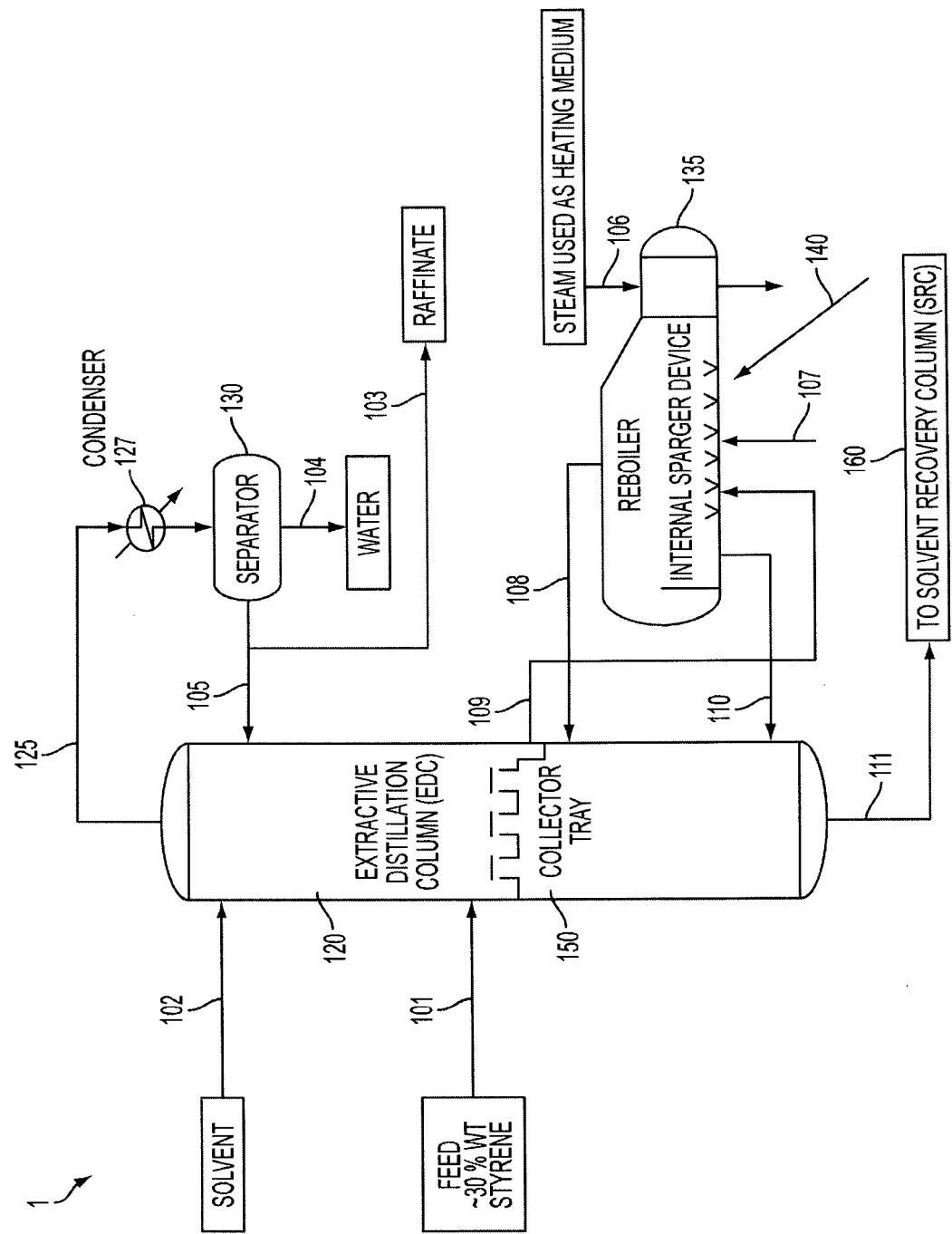

METHODS AND APPARATUSES FOR STEAM ADDITION TO A REBOILER COUPLED TO AN EXTRACTIVE DISTILLATION COLUMN FOR IMPROVED EXTRACTIVE DISTILLATION

CROSS-REFERENCE TO RELATED APPLICATIONS

This application claims priority to U.S. provisional patent application 61/239,272, filed Sep. 2, 2009, which is incorporated by reference herein in its entirety.

STATEMENT REGARDING FEDERALLY SPONSORED RESEARCH

Not applicable.

BACKGROUND

Adding live steam as stripping steam to a distillation column typically makes distillation operations possible at lower temperatures than without the added steam. Live steam can also be added when the distillation column is an extractive distillation column. Typically, the live steam is injected directly in the column shell below the last collector tray.

Incorporation of a reboiler into a distillation apparatus for use as a heating medium has numerous operational advantages, among which are making a distillation even possible. Although the use of reboilers is known in the art of distillation, the simultaneous use of a reboiler as both a heating medium for a distillation column and as a means for adding stripping steam in an extractive distillation process has not heretofore been described.

In view of the foregoing, improved methods and apparatuses for extractive distillation using a reboiler for both heating and for injection of stripping steam would have significant potential benefits in the art. Furthermore, reboilers having a modified design that allows for improved mass and heat transfer efficiency would also deliver significant benefits in the extractive distillation apparatuses and methods described herein.

SUMMARY OF THE INVENTION

In various embodiments, apparatuses for extractive distillation of an extract from a feed stream are described herein. The apparatuses include an extractive distillation column, a reboiler coupled to the extractive distillation column and a steam input line. The reboiler has an internal steam sparger device. The steam input line is coupled to the internal steam sparger device.

Other various embodiments of apparatuses for extractive distillation of an extract from a feed stream are also described herein. The apparatuses include an extractive distillation column, a kettle reboiler coupled to the extractive distillation column, a feed stream input line, a solvent input line, a steam input line, an output line for removing a mixture of distillate and solvent, and a steam output line. The kettle reboiler has an internal steam sparger device. The steam input line is coupled to the internal steam sparger device.

In other various embodiments, apparatuses for extractive distillation of an extract from a feed stream include an extractive distillation column, a reboiler coupled to the extractive distillation column and a steam input line. The reboiler has an interior space and an exterior surface. The steam input line is coupled to the interior space of the reboiler.

In other embodiments, methods for extractive distillation of an extract from a feed stream containing at least one hydrocarbon are described herein. The methods include a) extracting the at least one hydrocarbon from the feed stream using a solvent to form a hydrocarbon/solvent mixture, b) injecting stripping steam directly into a reboiler shell, c) adding steam as a heating medium into reboiler tubes, d) mixing the hydrocarbon/solvent mixture with the stripping steam through a steam sparger device located internally in the reboiler shell, and e) vaporizing the hydrocarbon/solvent mixture. In some embodiments, the methods further include separating the at least one hydrocarbon from the hydrocarbon/solvent mixture after the vaporizing step.

The foregoing has outlined rather broadly various features of the present disclosure in order that the detailed description that follows may be better understood. Additional features and advantages of the disclosure will be described hereinafter, which form the subject of the claims.

BRIEF DESCRIPTION OF THE DRAWING

For a more complete understanding of the present disclosure, and the advantages thereof, reference is now made to the following description to be taken in conjunction with the accompanying drawing describing specific embodiments of the disclosure, wherein:

FIG. 1 shows a schematic of an illustrative extractive distillation apparatus in which stripping steam is directly added to a reboiler.

DETAILED DESCRIPTION OF ILLUSTRATIVE EMBODIMENTS

In the following description, certain details are set forth such as specific quantities, concentrations, sizes, etc. so as to provide a thorough understanding of the various embodiments disclosed herein. However, it will be apparent to those of ordinary skill in the art that the present disclosure may be practiced without such specific details. In many cases, details concerning such considerations and the like have been omitted inasmuch as such details are not necessary to obtain a complete understanding of the present disclosure and are within the skills of persons of ordinary skill in the relevant art.

Referring to the drawing in general, it will be understood that the illustrations are for the purpose of describing particular embodiments of the disclosure and are not intended to be limiting thereto. Furthermore, drawings are not necessarily to scale.

While most of the terms used herein will be recognizable to those of ordinary skill in the art, it should be understood that when not explicitly defined, terms should be interpreted as adopting a meaning presently accepted by those of ordinary skill in the art. In cases where the construction of a term would render it meaningless or essentially meaningless, the definition should be taken from Webster's Dictionary, 3rd Edition, 2009. Definitions and/or interpretations should not be incorporated from other patent applications, patents, or publications, related or not, unless specifically stated in this specification or if the incorporation is necessary for maintaining validity.

As used herein, the term "aromatic" refers to aromaticity, a chemical property in which a conjugated ring of unsaturated bonds, lone pairs, or empty orbitals exhibit a stabilization stronger than would be expected by the stabilization of conjugation alone. It can also be considered a manifestation of cyclic delocalization and of resonance stabilization. This is usually considered to be because electrons are free to cycle around circular arrangements of atoms, which are alternately single- and double-bonded to one another.

As used herein, the term "aliphatic" refers to compounds having carbon atoms that are capable of being joined together in straight chains, branched chains, or rings (in which case they are called alicyclic). They can be joined by single bonds (alkanes), double bonds (alkenes), or triple bonds (alkynes).

In various embodiments, the methods and apparatuses described in the present disclosure make extractive distillation processes, particularly aromatic extractive distillation processes, more efficient. The various apparatuses and methods described herein utilize stripping steam injection into a reboiler coupled to an extractive distillation column of an extractive distillation apparatus to attain the improvement in efficiency. Such apparatuses and methods have been utilized in the recovery of styrene from untreated pyrolysis gasoline. Styrene produced by the methods and apparatuses described herein may be referred to hereinafter as GT-Styrene. One of ordinary skill in the art will recognize that hydrocarbons other than styrene may be extracted from a feed stream using the apparatuses and methods described herein. For example, other hydrocarbons may include BTX (benzene/toluene/xylenes), isoprene, butadiene and other vinyl aromatic compounds.

In the GT-Styrene extractive distillation process, hydrotreated C8 hydrocarbons, which include styrene, are heart-cut from a pyrolysis gasoline feed stream using an extractive distillation column (EDC). In a vapor-liquid operation, a solvent selectively extracts the styrene into the bottoms of the EDC, while rejecting other C8 aromatic compounds and non-aromatic components (i.e., aliphatic compounds) into a raffinate stream at the top of the EDC. The solvent can vary without limitation. In various embodiments, the EDC is a packed column. In various embodiments, the EDC operates under vacuum. Heat for the EDC is supplied from a reboiler using steam as the heating medium. The solvent enriched in styrene is withdrawn from the bottom of the EDC and is subsequently fed to a Solvent Recovery Column (SRC). The styrene is separated, and the solvent is thereafter sent back to the EDC.

In various embodiments, apparatuses for extractive distillation of an extract from a feed stream are described herein. The apparatuses include an extractive distillation column, a reboiler coupled to the extractive distillation column and a steam input line. The reboiler has an internal steam sparger device. The steam input line is coupled to the internal steam sparger device.

In other various embodiments, apparatuses for extractive distillation of an extract from a feed stream include an extractive distillation column, a reboiler coupled to the extractive distillation column and a steam input line. The reboiler has an interior space and an exterior surface. The steam input line is coupled to the interior space of the reboiler.

In some embodiments of the apparatuses, the extractive distillation column is a one-stage vaporization system. However, in other embodiments of the apparatuses, two-, three- or multi-stage vaporization systems may be formed by the extractive distillation column.

In some embodiments, of the apparatuses, the steam input line is a steam system generation loop. Such steam system generation loops provide for system water balance in an embodiment. For example, stripping steam originating from the system water balance (steam system generation loop) is injected at the bottom of the EDC to assist in the extractive distillation operation and to reduce the temperature at the bottom of the EDC. In some embodiments, vacuum effects are also combined with the steam addition at the bottom of the EDC to decrease the temperature. Water is subsequently transported from the EDC in raffinate phase, separated therefrom, and converted back into stripping steam in a closed loop process for further extractive operations. For the GT-Styrene extractive distillation process described herein, the lowering of temperature is particularly advantageous because polymerization of styrene on the EDC is eliminated or substantially reduced.

In various embodiments, the stripping steam injection is made directly at the base of the internal space of the reboiler. Such orientation of the steam injection advantageously provides for the highest mass/heat transfer efficiency of stripping steam injection. Other various modifications for injecting the stripping steam into the reboiler internal space also lie within the spirit and scope of the present disclosure. For example, injection of stripping steam below the last tray of the EDC (no reboiler present) or above the reboiler (below collector tray) will not have as high of a mass/heat transfer efficiency. In any of these other various embodiments, differential application of vacuum or increasing of the stripping steam addition rate, for example, may be used to improve the efficiency of the extractive distillation process.

In the various embodiments described herein, stripping steam injection into the reboiler may be used to facilitate the extraction of aromatic hydrocarbons. In various embodiments, the aromatic hydrocarbon is styrene or other vinyl aromatic compounds. However, the methods and apparatuses described herein may be used for extractive distillation of other distillates from feed streams while operating within the spirit and scope of the present disclosure. As referenced hereinabove, the apparatuses and methods of the present disclosure are advantageous in operating at temperatures at which polymerization of vinyl aromatic compounds is not promoted.

In various embodiments of the present disclosure, a kettle reboiler is used. However, one of ordinary skill in the art will recognize that any type of reboiler may be used in the methods and apparatuses described herein. Such alternative reboilers include, for example, thermosyphon reboilers and forced circulation reboilers. In the embodiments described herein, kettle reboilers advantageously provide a high residence time and low liquid entrainment for an extractive distillation process using injection of stripping steam directly into the interior space of the reboiler shell.

The reboiler may be modified to improve the efficiency of the extractive distillation process by using the calculated mass and heat transfer efficiency of the distillate. Although any size reboiler may be used in the present methods and apparatuses, the size of the reboiler should preferably, for highest efficiency, be sufficient to provide an effective residence time for a sufficient mass transfer to occur between the liquid phase and gas phase. An effective residence time depends, for example, on the composition of the feed stream being processed, and a person of ordinary skill in the art can readily determine an effective residence time depending on specific process requirements. In various embodiments, the reboilers of the present disclosure have been modified to also include an internal steam sparger device that advantageously provides for better steam distribution within the interior space of their shell.

In other various embodiments, apparatuses for extractive distillation of an extract from a feed stream include an extractive distillation column, a kettle reboiler coupled to the extractive distillation column, a feed stream input line, a solvent input line, a steam input line, an output line for removing a mixture of distillate and solvent, and a steam output line.

The kettle reboiler has an internal steam sparger device. The steam input line is coupled to the internal steam sparger device.

In other embodiments, methods for extractive distillation of an extract from a feed stream containing at least one hydrocarbon are described herein. The methods include a) extracting the at least one hydrocarbon from the feed stream using a solvent to form a hydrocarbon/solvent mixture, b) injecting stripping steam directly into a reboiler shell, c) adding steam as a heating medium into reboiler tubes, d) mixing the hydrocarbon/solvent mixture with the stripping steam through a steam sparger device located internally in the reboiler shell, and e) vaporizing the hydrocarbon/solvent mixture. In some embodiments, the methods further include separating the at least one hydrocarbon from the hydrocarbon/solvent mixture after the vaporizing step. In some embodiments, the reboiler shell is that of a kettle reboiler.

EXPERIMENTAL EXAMPLE

The following example is provided to more fully illustrate some of the embodiments disclosed hereinabove. It should be appreciated by those of ordinary skill in the art that the example that follows represents an exemplary mode for practice of the disclosure. Those of ordinary skill in the art should, in light of the present disclosure, appreciate that many changes can be made in the specific embodiments that are disclosed and still obtain a like or similar result without departing from the spirit and scope of the disclosure.

Example 1

Extractive Distillation Apparatus Containing a Reboiler

The various embodiments of the present disclosure will now be better understood by referring to FIG. 1. FIG. 1 shows a schematic of an illustrative extractive distillation apparatus 1 in which stripping steam is added directly to a reboiler. As shown in FIG. 1, a hydrotreated C8 feed stream (containing styrene) is heart-cut from pyrolysis gasoline and added to extractive distillation column 120 through feed stream input line 101. In the present example, the C8 heart cut is rich in styrene (~30 to ~40 wt. %). Extractive distillation column 120 is a packed column connected to feed stream input line 101 and solvent input line 102. In various embodiments, the extractive distillation apparatus is operated under a vacuum. In various embodiments, lean solvent is fed to extractive distillation column 120 through solvent input line 102 at a temperature range between about 70° C. and about 100° C.

Extractive distillation column 120 is coupled to kettle reboiler 135. Heat input into kettle boiler 135 is provided by saturated steam input line 106. The saturated steam condenses inside the reboiler tubes. In various embodiments, the temperature of the bottom of the extractive distillation column 120 is controlled, using kettle reboiler 135, to be about 120° C. or less. Such temperatures advantageously are relative non-conducive toward the polymerization of styrene in the column bottom.

In various embodiments of the extractive distillation apparatuses, in a vapor-liquid operation, the lean solvent extracts styrene into the bottom of extractive distillation column 120, while rejecting raffinate (other C8 aromatic hydrocarbons and non-aromatic hydrocarbons) to the overhead of the extractive distillation column 120. The column overhead vapors are condensed and sent to separator 130 through line 125, after passing through condenser 127. In separator 130, a water phase is removed by phase separation and passed through water removal line 104. The decanted water in water removal line 104 is pumped as process water through a steam system generation loop (not shown) and passed back to reboiler 135. Once at the reboiler 135, the water is converted into stripping steam, which enters the reboiler 135 through stripping steam line 107 at the base of the reboiler. In an embodiment, the hydrocarbon fraction (raffinate) remaining in separator 130 after water separation is pumped back to extractive distillation column 120 through reflux line 105, at reflux ratio of about 1. Alternately, raffinate may be drawn off from the system through raffinate removal line 103.

The stripping steam from stripping steam line 107 is sparged internally in reboiler 135 and mixed with liquid stream 109 from extractive distillation column 120. Afterward, vapor stream 108 generated by the stripping steam inside reboiler 135 is sent back to extractive distillation column 135 below collector tray 150. Vapor stream 108 provides lean solvent for continuing the extractive distillation process and further heats the extractive distillation column 120. The remaining liquid in reboiler 135 (containing styrene and solvent) is sent through reboiler line 110 as a liquid product to the column bottom. From there, the styrene plus solvent is pumped through line 111 to solvent recovery column 160.

The reboiler 135 is specially constructed for the extractive distillation processes of the present disclosure to provide an efficient extraction. As noted hereinabove, stripping steam is added to reboiler 135 through stripping steam line 107. Once in reboiler 135, the stripping steam enters internal sparging device 140. Addition of stripping steam advantageously lowers the partial pressure of the extracted styrene. Leaving reboiler 135, styrene plus solvent is sent as a liquid product through reboiler line 110 to the bottom of the extractive distillation column 120.

The styrene plus solvent stream in line 111 is sent to solvent recovery column 160, where the styrene is separated from solvent as pure product. Solvent is then sent back to the extractive distillation column 120 through line 102, as required.

As is known to one of ordinary skill in the art, the mass transfer efficiency of a stripping steam operation is defined as:

$$Ev = \frac{\text{actual partial pressure of material at outlet}}{\text{partial pressure of material if equilibrium prevails}}.$$

Mass transfer efficiency for reboilers is typically assumed to be 100% (close to one theoretical stage). However, 100% mass transfer efficiency is not applicable when stripping steam is added directly to a reboiler, especially for vertical reboilers where the residence time in the contacting zone (between the steam and liquid phase entering the reboiler) is not long enough. The kettle reboiler type described in the present embodiment of FIG. 1 was found to advantageously provide a high residence time (intimate contact) between phases. A model for estimate/calculate the efficiency was established, and this formed the basis for mechanical sizing and sparging apparatus of the reboiler.

From the foregoing description, one of ordinary skill in the art can easily ascertain the essential characteristics of this disclosure, and without departing from the spirit and scope thereof, can make various changes and modifications to adapt the disclosure to various usages and conditions. The embodiments described hereinabove are meant to be illustrative only and should not be taken as limiting of the scope of the disclosure, which is defined in the following claims.

What is claimed is the following:

1. An apparatus for extractive distillation of an extract from a feed stream, said apparatus comprising:
   an extractive distillation column;
   a reboiler coupled to the extractive distillation column, wherein the reboiler further comprises an internal steam sparger device;
   a steam input line coupled to the internal steam sparger device, and wherein the extract is an aromatic hydrocarbon; and
   a liquid stream line from the extractive distillation column coupled to the internal steam sparger device.

2. The apparatus of claim 1, wherein the extractive distillation column comprises a one-stage vaporization system.

3. The apparatus of claim 1, wherein the aromatic hydrocarbon is styrene.

4. The apparatus of claim 1, wherein the reboiler is a kettle reboiler.

5. An apparatus for extractive distillation of an extract from a feed stream, said apparatus comprising:
   an extractive distillation column;
   a kettle reboiler coupled to the extractive distillation column, wherein the kettle reboiler further comprises an internal steam sparger device;
   a feed stream input line;
   a solvent input line;
   a steam input line coupled to the internal steam sparger device;
   an output line for removing a mixture of distillate and solvent; and
   a liquid stream line from the extractive distillation column to the internal steam sparger device, wherein the extract is an aromatic hydrocarbon.

6. The apparatus of claim 5, wherein the extractive distillation column comprises a one-stage vaporization system.

7. The apparatus of claim 5, wherein the aromatic hydrocarbon is styrene.

8. The apparatus of claim 5, wherein the steam input line comprises a steam system generation loop.

9. An apparatus for extractive distillation of an extract from a feed stream, said apparatus comprising:
   an extractive distillation column;
   a reboiler coupled to the extractive distillation column, wherein the reboiler comprises an interior space and an exterior surface and further comprises an internal steam sparger device;
   a steam input line coupled to the internal steam sparger device; and
   a liquid stream line from the extractive distillation column to the internal steam sparger device, wherein the extract is an aromatic hydrocarbon.

10. The apparatus of claim 9, wherein the reboiler is selected from the group consisting of a kettle reboiler, a thermosyphon reboiler and a forced circulation reboiler.

* * * * *